United States Patent
Cheng et al.

(10) Patent No.: US 9,663,550 B2
(45) Date of Patent: May 30, 2017

(54) METHOD FOR PREPARING ABIRATERONE ACETATE

(71) Applicants: Wuhan Biocause Pharmaceutical Development Co., Ltd., Wuhan, Hubei (CN); Wuhan Biocause Pharmaceutical Co., Ltd., Wuhan, Hubei (CN)

(72) Inventors: Zhigang Cheng, Hubei (CN); Xuyong Dai, Hubei (CN); Xudong Wang, Hubei (CN); Shaokui Li, Hubei (CN); Liwei Li, Hubei (CN); Siyu He, Hubei (CN); Sen Cheng, Hubei (CN)

(73) Assignees: Wuhan Biocause Pharmaceutical Development Co., Ltd., Wuhan, Hubei (CN); Wuhan Biocause Pharmaceutical Co., Ltd., Wuhan, Hubei (CN)

( * ) Notice: Subject to any disclaimer, the term of this patent is extended or adjusted under 35 U.S.C. 154(b) by 0 days.

(21) Appl. No.: 15/030,018

(22) PCT Filed: Aug. 19, 2014

(86) PCT No.: PCT/CN2014/084702
§ 371 (c)(1),
(2) Date: Apr. 15, 2016

(87) PCT Pub. No.: WO2015/161590
PCT Pub. Date: Oct. 29, 2015

(65) Prior Publication Data
US 2016/0237109 A1    Aug. 18, 2016

(30) Foreign Application Priority Data

Apr. 21, 2014 (CN) .......................... 2014 1 0160153

(51) Int. Cl.
*C07J 43/00* (2006.01)
*C07J 1/00* (2006.01)
*C07J 31/00* (2006.01)

(52) U.S. Cl.
CPC ........... *C07J 43/003* (2013.01); *C07J 1/0011* (2013.01); *C07J 31/006* (2013.01)

(58) Field of Classification Search
CPC ...................................................... C07J 43/003
USPC ........................................................... 540/95
See application file for complete search history.

(56) References Cited

FOREIGN PATENT DOCUMENTS

| CN | 102030798 A | 4/2011 |
|---|---|---|
| CN | 101044155 B | 10/2012 |
| CN | 103172690 A | 6/2013 |
| CN | 103254265 A | 8/2013 |
| CN | 103965282 A | 8/2014 |
| WO | WO 93/20097 | 10/1993 |
| WO | WO 95/09178 | 4/1995 |
| WO | WO 2006/021777 A1 | 3/2006 |

*Primary Examiner* — Brenda Coleman
(74) *Attorney, Agent, or Firm* — Muncy, Geissler, Olds & Lowe, P.C.

(57) ABSTRACT

A method for preparing abiraterone acetate. The steps are: dehydroepiandrosterone acetate and trifluoromethanesulphonic anhydride undergo a sulfonylation reaction under the catalysis of an organic base to obtain a compound as represented by formula II; the compound is reacted with a 3-pyridine organoboron compound or a 3-pyridine organosilicone compound under the catalysis of Bis(triphenylphosphine) palladium(II) dichloride to obtain a crude abiraterone acetate product; the crude product is recrystallized in a protic or aprotic solvent to obtain an abiraterone acetate crystal; the crystal is further put into a solvent which easily dissolves the crystal and dissolved under heating, and the solution is dropwise added into a solvent which does not easily dissolve the crystal until a solid is precipitated under stirring, such that a micro powder abiraterone acetate is obtained; and the solvent which easily dissolves the crystal is a mixture of any two or more of acetone, ethanol and water, and the solvent which does not easily dissolve the crystal is water. The method has a rational route, a simple and convenient operation, a good product quality, and a high yield. No column chromatography, and salt-formation are required in the entire process to satisfy requirements of industrial scale productions. Furthermore, an abiraterone acetate particle size of about 10 um is obtained.

9 Claims, No Drawings

METHOD FOR PREPARING ABIRATERONE ACETATE

TECHNICAL FIELD

The present invention relates to the field of fine chemical or pharmaceutical chemical products, in particular to the synthesis, production and powder crystallization processes of new cancer drug abiraterone acetate.

BACKGROUND

The chemical name of abiraterone acetate (CAS: 154229-18-2) is (3β)-17-(3-pyridyl)-androst-5,16-dien-3-ol acetate, the formula is:

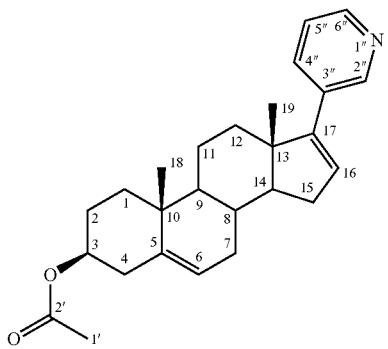 [SMILES: CC(=O)O[C@H]1CC[C@@]2(C)C(=CCC3C2CC[C@]2(C)C(c4cccnc4)=CCC32)C1]

Abiraterone acetate is an inhibitor of CYP17 suitable for, in combining with prednisone, the treatment of refractory prostate cancer patients who have failed treatment with docetaxel-containing [docetaxel] chemotherapy transfer by. For prostate cancer patients, the male hormone testosterone stimulates the growth of prostate tumors. Medical or surgical treatment is adopted to reduce the generation of testosterone or prevent testosterone.

According to the published literatures, there are two kinds of abiraterone acetate synthesis.

The first method (WO9320097, WO2006021777, CN102030798, CN101044155) is as follows: With dehydroepiandrosterone acetate as a starting material, obtaining triflate ester through one-step synthesis, obtaining crude abiraterone acetate through SUZUKI reaction with diethyl (3-pyridyl) borane, and then the crude product is purified by column chromatography or by salt-formation with methanesulfonic acid/trifluoromethanesulfonic acid to obtain abiraterone acetate.

Defects of this Method:

(1) Different solvents are used in steps 1 and 2, which results in difficult work-up and high cost;

(2) The purification is done through column chromatography or salification with methanesulfonic acid/trifluoromethanesulfonic acid to obtain abiraterone acetate, which increases production steps and costs.

The second method (WO9509178, Chinese Journal of Pharmaceuticals, 2012, 43 (10), 804-806) is as follows: Dehydroepiandrosterone as the starting material reacts with hydrazine hydrate to obtain Dehydroepiandrosterone-17-hydrazone, which undergoes an iodization with iodine and then a Suzuki coupling reaction with (3-pyridyl)-diethyl borane to obtain abiraterone, followed by esterification with acetyl chloride to obtain abiraterone acetate.

Defects of this method: More reaction steps are needed and more solvents are used, which increases the manufacturing steps and costs.

DISCLOSURE OF THE INVENTION

In order to solve the above problems in the prior art, the present invention provides a synthesis process featured by reasonable route, easy operation, good product quality and high yield. The whole process does not need purification by column chromatography or salt-formation, which meets the needs of industrial-scale production, and meanwhile abiraterone acetate of particle size of about 10 μm is obtained.

The method provided in present invention for preparing abiraterone acetate uses dehydroepiandrosterone acetate (Formula I), 3-pyridine organoboron compound or 3-pyridyl organic silicon compound as the basic raw material, and synthesizes abiraterone acetate through the following 2-step reaction:

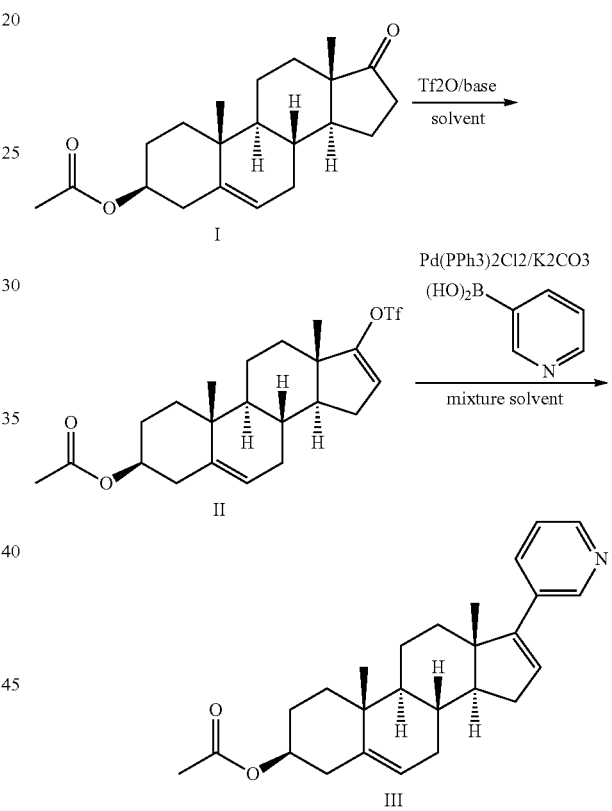

The specific preparation method comprises the following steps:

(1) Dehydroepiandrosterone acetate reacting with Trifluoromethanesulfonic anhydride in the presence of organic base as catalyst at −30~50° C. for 1-72 hours to obtain a compound as shown in Formula II;

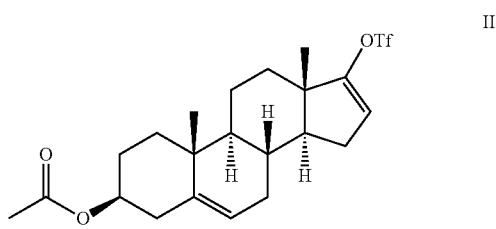

(2) The compound of Formula II reacting with 3-pyridine organoboron compound or 3-pyridine organosilicon compound in the presence of Bis(triphenylphosphine) palladium (II) dichloride as catalyst at 5~150° C. for 1-72 hours to obtain crude abiraterone acetate;

(3) The crude abiraterone acetate recrystallizing in proton or non-proton solvent, in the mass-volume ratio of crude abiraterone acetate to proton or non-proton solvent is 1:10-30 at −10~30° C. to obtain abiraterone acetate crystal;

(4) Putting abiraterone acetate crystals into soluble solvent and heating to dissolve, then dripping it to insoluble solvent, controlling the stirring speed, temperature and amount of solvent, to precipitate solids to obtain micronized abiraterone acetate; said soluble solvent is a mixture of any two or more of acetone, ethanol and water; said insoluble solvent is water.

Preferably, in step (1), the reaction temperature is −20~20° C., and reaction time is 3~10 h.

TABLE 1

| Reaction temperature | Reaction time | Reaction ratio (HPLC) (Product: raw materials) | Product purity(HPL C) |
|---|---|---|---|
| −20-20° C. | 0~3 h | <2.0 | <50% |
|  | 3~10 h | >4.0 | >75% |
|  | >10 h | >4.0 | <75% |
| <−20° C. | 0~3 h | <4.0 | <50% |
|  | 3~10 h | <1.0 | <50% |
|  | >10 h | <2.0 | <50% |
| >20° C. | 0~3 h | <4.0 | <75% |
|  | 3~10 h | >4.0 | <50% |
|  | >10 h | >4.0 | <50% |

Table 1 shows the impact on reaction ratio of product and raw materials and the purity of the product through only adjusting the reaction temperature and time in step (1) with the other conditions unchanged, and from Table 1, to ensure a high reaction ratio and a high purity, the preferred reaction temperature is −20~20° C., and reaction time is 3~10 h.

Preferably, in step (2), the reaction time is 4-24 hours, and the reaction temperature is 60~130° C.

TABLE 2

| Reaction time | Reaction temperature | Content of raw material (HPLC) in Step (2) | Product purity(HPLC) |
|---|---|---|---|
| 4~24 h | 0~60° C. | >20% | <80% |
|  | 60~130° C. | <1% | >90% |
|  | >130° C. | <1% | <90% |
| 0~4 h | 0~60° C. | >90% | <10% |
|  | 60~130° C. | >10% | <90% |
|  | >130° C. | <5% | <50% |
| >24 h | 0~60° C. | >10% | <80% |
|  | 60~130° C. | <1% | <90% |
|  | >130° C. | <1% | <90% |

Table 2 shows the impact on content of raw material and the purity of the product through only adjusting the reaction temperature and time in Step (2) with the other conditions unchanged, and from Table 2, to achieve complete reaction of raw material in Step (2) as much as possible and to increase product purity, the preferred reaction time is 4~24 h and reaction temperature is 60~130° C.

Preferably, in Step (3), the mass-volume ratio is 1:10-20, and the recrystallization temperature is −5~10° C.

Preferably, in Step (4), the process of stirring to precipitated solid includes: controlling the stirring speed at 300-450 rpm, and temperature at 0~15° C.; mass-volume ratio of abiraterone acetate crystals to soluble solvent is 1:10-30; mass-volume ratio of abiraterone acetate crystals to insoluble solvent is 1:10-30

Preferably, said organic base in Step (1) is methylamine, ethylamine, diethylamine, triethylamine, pyridine, 2-methylpyridine, 2,6-dimethyl-pyridine, quinoline, isoquinoline, piperidine, piperazine, nitrogen-containing organic base compound, sodium carbonate, potassium carbonate and potassium phosphate, or a mixture thereof.

Preferably, said organic base in Step (1) is 2-methylpyridine, quinoline or a mixture of both, and the molar ratio of both in the mixture is 1:1.

Preferably, said 3-pyridine organoboron compound is: 3-pyridylboronic acid, Potassium 3-Pyridyltrifluoroborate, Pyridine-3-boronic acid pinacol ester and 3-(5,5-dimethyl-1,3,2-dioxaborinan-2-yl)pyridine, or a mixture thereof; said 3-pyridine organosilicon compound is 3-Trimethoxysilyl-pyridine.

Preferably, said proton or non-proton solvent is: water, methanol, ethanol, tetrahydrofuran, acetonitrile, acetone, dioxane, petroleum ether, toluene, dimethyl formamide and dimethyl acetamide, or a mixture thereof.

Preferably, said Step (1) reacts in a proton or non-proton solvent, and Step (2) reacts under protection of nitrogen.

As compared with the prior art, the present invention has the following advantages:

1. Reaction conditions are mild, and the product in Step (1) can directly go into the next reaction without isolation;
2. The raw materials are easily available with low total cost;
3. Purification by column chromatography or salt-formation is not needed, which is suitable for industrial production.
4. About 10 μm of micronized products obtained by the crystallization process.

DETAILED DESCRIPTION

With regard to detailed description and technical content of the present invention, please refer to the following detailed description and the accompanying drawings described below. Drawings and detailed description are only for instructions, not limited to the present invention.

Below is a further illustration of the present invention in conjunction with the specific embodiments so that those skilled in the art may better understand and implement the present invention, but the cited embodiments do not limit the present invention.

Example 1 Preparation of Abiraterone Acetate

1. In a dry 500 mL reaction flask, adding 10 g (30.3 mmol) of dehydroepiandrosterone acetate and 100 mL of tetrahydrofuran; cooling to 0° C., then slowly dripping 5.6 mL (33.3 mmol) of trifluoromethanesulfonic anhydride, after addition, then dripping 3.0 mL (30.6 mmol) of 2-methyl pyridine with maintaining the temperature below 5° C., after addition, keeping reacting for 2 hours at 0° C., heating to room temperature after completion of reaction, and stirring for 3 hours at constant temperature, going directly to the next step.

2. Under nitrogen atmosphere, cooling the reaction liquid of previous step to −5° C., adding 20 mL of potassium carbonate aqueous solution (including potassium carbonate 15.2 g, 110 mmol), keeping the temperature not higher than 5° C., then adding 97 mg (0.14 mmol) of Bis(triphenylphosphine) palladium(II) dichloride(Pd(PPh3)2Cl2), and 5.1 g (41.5 mmol) of 3-pyridylboronic acid, heating to reflux and keeping reacting overnight. With HPLC monitoring of complete reaction of the product in Step 1, adding 300 mL of ethyl acetate for extraction in 3 times (each 100 mL), combining the organic phase, washing the organic phase with 60 mL of water in 3 times (each 20 mL), drying with anhydrous magnesium sulfate, filtering and concentrating to obtain 8.2 g of yellow solid, i.e. crude abiraterone acetate (III), with the yield of 69%.

3. Dissolving the above 8.2 g crude Abiraterone Acetate (III) in 120 ml of mixture of ethanol and petroleum ether (volume ratio 1:1) by heating, adding 0.5 g of activated carbon and refluxing for 30 minutes. The flask contents were filtered and the filtrate was cooled to allow crystallization to obtain 4.5 g Abiraterone Acetate (III) crystals, with the yield of 55%. $^1$HNMR (d-CDCl$_3$) δ: 1.047 (s, 3H, 19-CH$_3$), 1.084 (s, 3H, 18-CH$_3$), 1.12-1.19 (m, 1H, 1-CH), 1.483 (s, 1H, 1-CH), 1.155-1.165 (m, 1H, 11-CH), 1.631-1.788 (m, 8H, 2-CH$_2$, 8-CH, 9-CH, 11-CH, 12-CH$_2$, 14-CH), 1.862-1.891 (m, 2H, 7-CH$_2$), 2.033-2.053 (m, 2H, 4-CH, 15-CH), 2.046 (s, 3H, 1'-CH$_3$), 2.335 (m, 1H, 4-CH), 2.361 (m, 1H, 15-CH), 4.605-4.633 (m, 1H, 3-CH), 5.417-5.429 (d, 1H, 6-CH), 5.992-6.005 (d, 1H, 16-CH), 7.210-7.278 (m, 1H, 5"-CH), 7.637-7.666 (m, 1H, 4"-CH), 8.451-8.467 (m, 1H, 6"-CH), 8.617-8.621 (d, 1H, 2"-CH); $^{13}$C-NMR (d-CDCl3) δ: 16.410 (1'-C), 19.089 (19-C), 20.651 (11-C), 21.261 (18-C), 27.571 (2-C), 30.227 (7-C), 31.336 (1-C), 31.621 (15-C), 35.028 (8-C), 36.602 (10-C), 36.746 (12-C), 37.970 (4-C), 47.134 (13-C), 50.079 (9-C), 57.285 (14-C), 73.654 (3-C), 122.108 (6-C), 122.836 (5"-C), 129.005 (16-C), 132.732 (4"-C), 133.459 (3"-C), 139.842 (5-C), 147.756 (2",6"-C), 151.487 (17-C), 170.283 (2'-C); MS (m/z) 392.3 (M+1)

Example 2 Preparation of Abiraterone Acetate

1. In a dry 500 mL reaction flask, adding 10 g (30.3 mmol) of dehydroepiandrosterone acetate and 100 mL of toluene, cooling to below −5° C., then slowly dripping 5.6 mL (33.3 mmol) of trifluoromethanesulfonic anhydride, after addition, then dripping the mixture of 1.5 mL (15.3 mmol) of 2-picoline and 1.9 mL (15.3 mmol) of quinoline, and stirring for 3~3.5 h at the constant temperature of −5° C., the reaction liquid color turning brown; increasing the temperature to 10° C., stirring at constant temperature for 2~2.5 h, the reaction liquid color turning tan. After completion of the reaction, adding 150 mL of water until quenching reaction occurs in the reaction flask and stirring for 10 minutes to separate the organic layer; extracting the aqueous phase with 50 mL of toluene, and combining the organic phase; washing the organic layer once with 50 mL of water, and then washing three times with saturated brine (50 mL×3); the organic layer is separated, and goes directly to the next feeding.

2. Under nitrogen atmosphere, adding 30 mL of aqueous solution of potassium carbonate (including potassium carbonate 15.2 g, 110 mmol) to the reaction liquid in the previous step, then adding 97 mg (0.14 mmol) of Pd(PPh3) 2Cl2, and 5.1 g (41.5 m mol) of 3-pyridine boronic acid, then adding 20 mL of absolute ethanol, heating to reflux, and reacting overnight. After the reaction, cooling the reaction liquid to room temperature, separating the layers, discarding the lower aqueous phase, washing the upper organic phase with 60 mL of drinking water, then separating the lower aqueous phase, collecting the organic phase, then washing the organic layer with 30 mL of drinking water three times (each time 10 mL) and washing the organic layer with 30 mL of saturated brine; separating the organic layer, adding a small amount of activated carbon and appropriate amount of anhydrous MgSO$_4$ to the separated organic layer to dry for 30 min, making suction and filtration, and concentrating the filtrate at 60° C. under reduced pressure to obtain a crude Abiraterone acetate.

3. Adding abiraterone acetate crude to 120 mL of acetonitrile reflux clear solution, and stirring at room temperature for crystallization to obtain abiraterone acetate crystals (III) 4.5 g, with the yield of 38%.

4. Heating and dissolving 4.5 g of crude abiraterone acetate (III) in 70 mL of mixture of ethanol and petroleum ether (volume ratio 1:1), adding 0.3 g of activated carbon to reflux for 30 minutes and filtering. After filtrate cooling and crystallization, 4.5 g of abiraterone acetate (III) crystals can be obtained, with the yield of 78%.

Example 3 Scale-up Production Process of Abiraterone Acetate

1. In a dry 100 L reaction flask, adding 20 L of toluene, then adding 4 kg (12.12 mol) of dehydroepiandrosterone acetate and stirring; cooling to below −5° C., slowly dripping 2240 mL (13.32 mol) of trifluoromethanesulfonic anhydride, the reaction liquid color turning light green; after addition of trifluoromethanesulfonic anhydride, stirring 10-15 min at a temperature below −5° C., then dripping 11.36 L of toluene solution of 2-picoline and quinoline (containing 600 m (16.12 mol) of 2-picoline, and 760 mL (16.12 mol) of quinoline, and 10 L of toluene). After addition, stirring 3~3.5 h at the constant temperature of −5° C., the reaction liquid color turning brown; heating to 10° C., stirring at constant temperature for 2~2.5 h, the reaction liquid color turning tan. After completion of the reaction, adding 60 L of water until quenching reaction occurs in the reactor and stirring for 10 minutes to separate the organic layer; extracting the aqueous phase with 10 L of toluene, and combining the organic phase; washing the organic layer once with 20 L of water, and then washing three times with saturated brine (20 L×3); the organic layer is separated, and goes directly to the next feeding.

2. Under nitrogen atmosphere, adding about 40 L of reaction liquid of previous step to 100 L reactor, at room temperature, adding 38.8 g (56.0 mmol) of Pd(PPh3)2Cl2, and 1.6 kg (13.0 mol) of 3-pyridine boronic acid and 3.8 kg (27.5 mol) of potassium carbonate in turn, 22 L of absolute ethanol and 16 L of drinking water in turn, heating to reflux, the reaction liquid turning brown, and stirring for 5 h. After the reaction, cooling the reaction liquid to room temperature, separating the layers, discarding the lower aqueous phase, washing the upper organic phase with 24 L of drinking water, stirring for layering, then separating the lower aqueous phase, collecting the organic phase, then washing the organic layer with 120 L of drinking water three times (each time 30 L) and washing the organic layer with 40 L of saturated brine; separating the organic layer, adding 0.5 Kg of activated carbon and 4 Kg of anhydrous MgSO$_4$ to the separated organic layer to dry for 30 min, making suction and filtration, and concentrating the filtrate at 60° C. under reduced pressure to obtain 5500±1000 g of brown oily crude Abiraterone acetate.

3. Adding 16 L of acetonitrile to the above oily material, heating to 50° C., stirring until the solution is clear, naturally cooling to room temperature, stirring at room temperature to crystallize, making suction and filtration, and washing the filter cake with 2 L of cold acetonitrile; drying the filter cake at 60° C. for 4-6 hours to obtain 2000±300 g crude product.

Adding the dried crude product to 30 L reactor, then adding 24 L acetonitrile, stirring at 60~65° C. until the solution is clear, then adding 0.2 kg of activated carbon, continue stirring for 15 min, filtering when it is hot, transferring the filtrate to 50 L reactor, stirring at room temperature to allow crystallization, then cooling at 0±5° C. to allow crystallization for 1.5~2 h, making suction and filtration, washing the filter cake with 2 L of cold acetonitrile, at 55~65° C., drying 4-6 hours to obtain 1600±300 g of abiraterone acetate crystals, with the yield of 34%.

4. Adding to 50 L reactor 16 L of purified water and 4.6 L of acetone, cooling to 0~5° C., controlling the stirring speed at 300-450 rpm, then adding rapidly 27.4 L of acetone solution in which 1600 g of abiraterone acetate crystal is dissolved at 30~35° C., keeping the temperature below 15° C. After addition, maintaining the temperature at 0~5° C., stirring rapidly for 1 h, making suction and filtration, washing the filter cake with 2 L of ice aqueous acetone (volume ratio of acetone to water is 2:1), and dry. At 60~70° C., drying in vacuum for 24 h to obtain 1500 g of dry fine product in a particle size of about 10 μm, i.e. micronized abiraterone acetate, with the yield of 94%.

Preferred embodiments are only illustrative of the above described embodiments, and the scope of the present invention is not limited thereto. Equivalent or conversion made by those skilled in the art on the basis of the present invention is within the scope of the present invention. The protection scope of the present invention is based on the claims.

The invention claimed is:

1. A method for preparing abiraterone acetate, comprises the following steps:
   (1) Dehydroepiandrosterone acetate reacting with Trifluoromethanesulfonic anhydride in the presence of organic base as catalyst at −30~50° C. for 1-72 hours to obtain a compound as shown in Formula II;

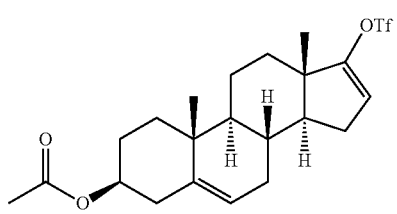

(2) the compound of Formula II reacting with 3-pyridine organoboron compound or 3-pyridine organosilicon compound in the presence of Bis(triphenylphosphine) palladium(II) dichloride as catalyst at 5~150° C. for 1-72 hours to obtain crude abiraterone acetate;
   (3) the crude abiraterone acetate recrystallizing in proton or non-proton solvent, in the mass-volume ratio of crude abiraterone acetate to proton or non-proton solvent is 1:10-30 at 10~30° C. to obtain abiraterone acetate crystal; and
   (4) putting abiraterone acetate crystals into soluble solvent and heating to dissolve, then dripping it to insoluble solvent, controlling the stirring speed, temperature and amount of solvent, to precipitate solids to obtain micronized abiraterone acetate;
   said soluble solvent is a mixture of any two or more of acetone, ethanol and water; said insoluble solvent is water.

2. The method for preparing abiraterone acetate according to claim 1, characterized in that in wherein Step (1), the reaction temperature is −20~20° C., and reaction time is 3~10 h.

3. The method for preparing abiraterone acetate according to claim 1, wherein Step (2), the reaction time is 4~24 h and the reaction temperature is 60~130° C.

4. The method for preparing abiraterone acetate according to claim 1, wherein Step (3), the mass-volume ratio is 1:10-20, and the recrystallization temperature is −5~10° C.

5. The method for preparing abiraterone acetate according to claim 1, wherein Step (4), the process of stirring to precipitated solid includes: controlling the stirring speed at 300-450 rpm, and temperature at 0~15° C.; mass-volume ratio of abiraterone acetate crystals to soluble solvent is 1:10-30; mass-volume ratio of abiraterone acetate crystals to insoluble solvent is 1:10-30.

6. The method for preparing abiraterone acetate according to claim 1, wherein said organic base in Step (1) is methylamine, ethylamine, diethylamine, triethylamine, pyridine, 2-methylpyridine, 2,6-dimethyl-pyridine, quinoline, isoquinoline, piperidine, piperazine, nitrogen-containing organic base compound, sodium carbonate, potassium carbonate and potassium phosphate, or a mixture thereof.

7. The method for preparing abiraterone acetate according to claim 6, wherein said organic base in Step (1) is 2-methylpyridine, quinoline or a mixture of both, and the molar ratio of both in the mixture is 1:1.

8. The method for preparing abiraterone acetate according to claim 1, wherein said 3-pyridine organoboron compound is: 3-pyridylboronic acid, Potassium 3-Pyridyltrifluoroborate, Pyridine-3-boronic acid pinacol ester and 3-(5,5-dimethyl-1,3,2-dioxaborinan-2-yl)pyridine, or a mixture thereof; said 3-pyridine organosilicon compound is 3-Trimethoxysilyl-pyridine.

9. The method for preparing abiraterone acetate according to claim 1, wherein said proton or non-proton solvent is: water, methanol, ethanol, tetrahydrofuran, acetonitrile, acetone, dioxane, petroleum ether, toluene, dimethyl formamide and dimethyl acetamide, or a mixture thereof.

* * * * *